United States Patent [19]

Takahashi et al.

[11] Patent Number: 4,625,042
[45] Date of Patent: Nov. 25, 1986

[54] PROCESS FOR PREPARING 6-FLUORO-4-CHROMANONE USING 3-(4-FLUOROPHENOXY)PROPIONITRILE

[75] Inventors: Satomi Takahashi, Kobe; Yasuyoshi Ueda, Takasago; Yoshio Shimada, Kakogawa; Kiyoshi Watanabe, Akashi, all of Japan

[73] Assignee: Kanegafuchi Kagaku Kogyo Kabushiki Kaisha, Osaka, Japan

[21] Appl. No.: 752,439

[22] Filed: Jul. 8, 1985

[30] Foreign Application Priority Data

Jul. 9, 1984 [JP] Japan .................................. 59-142875

[51] Int. Cl.⁴ .................... C07D 311/22; C07C 121/75
[52] U.S. Cl. ........................................ 549/401; 558/389
[58] Field of Search .................... 260/465 F; 549/401; 558/389

[56] References Cited

U.S. PATENT DOCUMENTS

| | | | |
|---|---|---|---|
| 2,819,197 | 1/1958 | Santmyer et al. .................... | 514/520 |
| 2,974,160 | 3/1961 | Heininger ........................ | 260/465 F |
| 3,467,692 | 9/1969 | Newallis et al. ................. | 260/465 F |
| 4,117,230 | 9/1978 | Sarges ................................ | 548/309 |
| 4,130,714 | 12/1978 | Sarges ................................ | 548/309 |

*Primary Examiner*—Dolph H. Torrence
*Attorney, Agent, or Firm*—Armstrong, Nikaido, Marmelstein & Kubovcik

[57] ABSTRACT

The present invention relates to 3-(4-fluorophenoxy)-propionitrile having the formula (I):

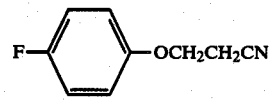

(I)

a process for preparing 3-(4-fluorophenoxy)propionitrile having the formula (I) which comprises reacting 4-fluorophenol and acrylonitrile in the presence of a tertiary amine, a process for preparing 6-fluoro-4-chromanone having the formula (II):

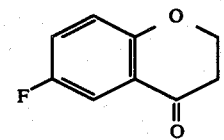

(II)

which comprises reacting 3-(4-fluorophenoxy)propionitrile having the formula (I) with an acid, and a process for preparing 6-fluoro-4-chromanone having the formula (II) which comprises reacting 4-fluorophenol with acrylonitrile in the presence of a catalyst to give 3-(4-fluorophenoxy)propionitrile having the formula (I), which is then reacted with an acid. 6-Fluoro-4-chromanone is an important intermediate for the synthesis of (S)-2,3-dihydro-6-fluoro-spiro[4H-1-benzopyran-4,4'-imidazolidine]-2',5'dione (USAN: sorbinil).

6 Claims, No Drawings

PROCESS FOR PREPARING 6-FLUORO-4-CHROMANONE USING 3-(4-FLUOROPHENOXY)PROPIONITRILE

BACKGROUND OF THE INVENTION

The present invention relates to 3-(4-fluorophenoxy)-propionitrile having the formula (I):

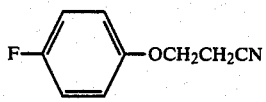
(I)

and a process for preparing the same. The present invention also relates to a process for preparing 6-fluoro-4-chromanone having the formula (II):

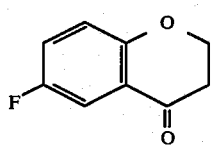
(II)

starting from 3-(4-fluorophenoxy)propionitrile having the formula (I).

6-Fluoro-4-chromanone having the formula (II) is an important intermediate for synthesis of (S)-2,3-dihydro-6-fluoro-spiro[4H-1-benzopyran-4,4'-imidazolidine]-2',5'-dione (USAN: sorbinil) having the formula (III):

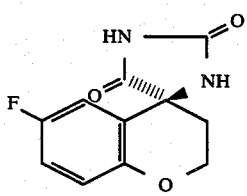
(III)

which is expected to be a novel remedy for a complication of diabetes based on the high activity of aldose reductase inhibition, and can be easily converted into (RS)-2,3-dihydro-6-fluoro-spiro[4H-1-benzopyran-4,4'-imidazolidine]-2',5'-dione by Bucherer reaction where the reaction is carried out with heating in the presence of sodium cyanide and ammonium carbonate. 3-(4-Fluorophenoxy)propionitrile is a useful intermediate for synthesis of said 6-fluoro-4-chromanone. Similar compounds such as 3-phenoxypropionitrile, 3-(4-chlorophenoxy)propionitrile and 3-(4-tolyloxy)propionitrile have been known except the compound of the present invention.

Hitherto, 6-fluoro-4-chromanone having the formula (II) has been prepared by Williamson's synthesis, i.e. reacting 4-fluorophenol and 3-chloropropionic acid in the presence of sodium hydroxide to form 3-(4-fluorophenoxy)propionic acid having the formula (IV), which is then warmed in polyphosphoric acid (U.S. Pat. No. 4,117,230 and U.S. Pat. No. 4,130,714). The process is shown in the following scheme:

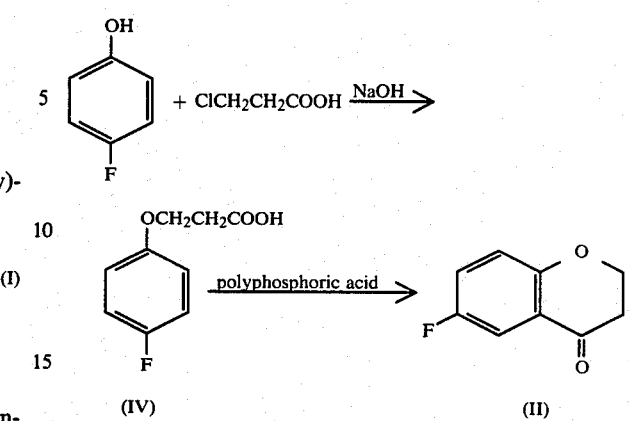

However, side reaction where 3-chloropropionic acid is decomposed into 3-hydroxypropionic acid exceed the formation of 3-(4-fluorophenoxy)propionic acid having the formula (IV) from 4-fluorophenol and therefore yield of the compound (IV) is still quite low even if great excess of 3-chloropropionic acid is employed (J. Amer. Chem. Soc., 81, 94 (1959)). Thus, the above process cannot be effective for an industrial production of 6-fluoro-4-chromanone having the formula (II), considering a high price of 4-fluorophenol as a starting material.

As the result of the continuous efforts of the present inventors to establish a novel, economical, easily operated and safe process for an industrial production of 6-fluoro-4-chromanone having the formula (II), it was found that 6-fluoro-4-chromanone having the formula (II) could be effectively synthesized by a formation of ether linkage due to cyanoethylation reaction where 4-fluorophenol is reacted with acrylonitrile in the presence of catalyst to give 3-(4-fluorophenoxy)propionitrile having the formula (I), which is either converted into 6-fluoro-4-chromanimine having the formula (V) in polyphosphoric acid and then hydrolyzed, or first subjected to acid hydrolysis to form 3-(4-fluorophenoxy)propionic acid having the formula (IV) and then dehydrated to cyclize in mineral acid such as polyphosphoric acid.

Hitherto, cyanoethylation of phenolic compounds has been carried out in the presence of strong base such as trimethylbenzylammonium hydroxide (Triton B), metallic sodium and sodium methoxide (J. Chem. Soc., 920 (1945), J. Amer. Chem. Soc., 70, 599 (1948), Bull. Soc. Chim. France, 1288 (1957), and the like), in the presence of copper compounds (U.S. Pat. No. 2,974,160) or in the presence of anhydrous aluminum chloride-dried HCl (J. Org. Chem, 22, 1264 (1957)).

As the result of the continuous efforts of the present inventors to establish catalysts effective in the reaction between 4-fluorophenol and acrylonitrile, it was found that copper compounds, especially cupric hydroxide, cupric acetate monohydrate, and the like were excellent catalysts and organic amine, which has not been described as catalyst of cyanoethylation reaction, especially tertiary amine such as triethylamine also could be a particularly effective catalyst in this reaction. Further, it was found that thus obtained 3-(4-fluorophenoxy)propionitrile having the formula (I) could be effectively utilized for a synthesis of 6-fluoro-4-chromanone having the formula (II).

DETAILED DESCRIPTION

The process of the present invention can be shown in the following scheme:

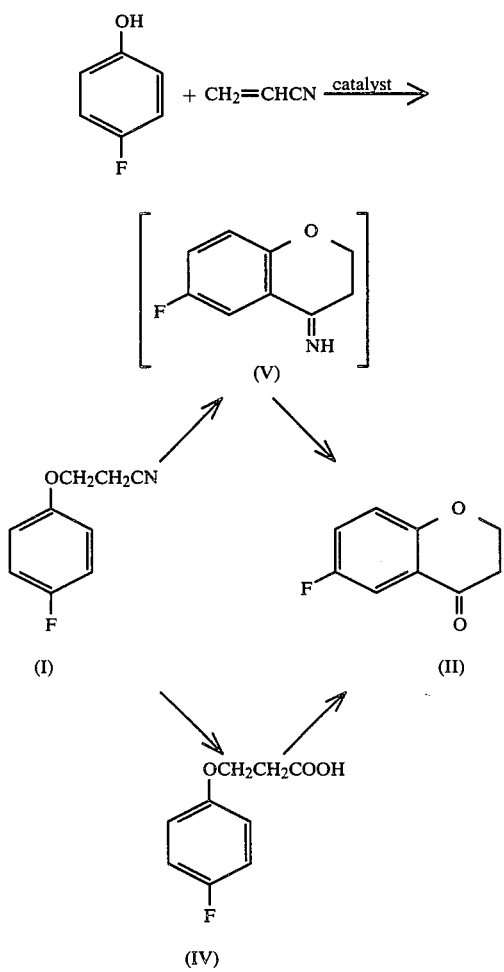

The first reaction of the present invention is the cyanoethylation of 4-fluorophenol in the presence of a proper catalyst to form ether bond. Examples of a catalyst which is effectively used in this reaction are copper compound such as cupric hydroxide, cupric acetate, cupric acetate monohydrate, cupric carbonate and cupric oxide; powdered copper; tertiary amine such as trimethylamine, triethylamine, tri-n-butylamine, tri-n-octylamine and dimethylcyclohexylamine; potassium hydroxide; barium hydroxide; and zinc hydroxide. Tertiary amine such as triethylamine is preferably used in the industrial production since the reaction can be conducted in a high yield, with a simple operation after the reaction such as removing catalyst and in a low cost.

Conditions for the reaction cannot be sweepingly determined since they vary depending on the kinds of a catalyst. However, a catalyst is generally used in such an amount as more than 0.01 times mole, preferably around 0.1 to around 0.5 times mole based on 4-fluorophenol. Acrylonitrile is preferably used in an excess amount based on 4-fluorophenol. However, about 2 to 3 times mole of acrylonitrile based on 4-fluorophenol is sufficient. Though acrylonitrile also works as a solvent, nonpolar solvent such as benzene and toluene or polar solvent such as water and ethanol can be used if necessary. When acrylonitrile is used as a solvent, the reaction temperature is preferably around a reflux temperature and thereby the reaction is completed in about 6 to 16 hours. If the reaction temperature is below a reflux temperature, the reaction rate is lowered and further reaction time may be required until the reaction is completed. After completion of the reaction, an excess amount of acrylonitrile, solvent and tertiary amine and some quantity of unreacted 4-fluorophenol can be removed by distillation under reduced pressure. When a catalyst of solid form is employed, it must be removed by filtration. Thus obtained 3-(4-fluorophenoxy)propionitrile having the formula (I) can be used in the following reaction as it is, and also it can be separated in a high yield in an almost pure form by washing with a solution of sodium hydroxide of a proper concentration.

3-(4-Fluorophenoxy)propionitrile having the formula (I) can be converted into 6-fluoro-4-chromanone having the formula (II) by two pathways. In one pathway, 3-(4-fluorophenoxy)propionitrile having the formula (I) is subjected to the ring closure reaction to form 6-fluoro-4-chromanimine, which is then hydrolyzed into 6-fluoro-4-chromanone. In the other pathway, 3-(4-fluorophenoxy)propionitrile having the formula (I) is hydrolyzed into 3-(4-fluorophenoxy)propionic acid having the formula (IV), which is then dehydrated to cyclize to give 6-fluoro-4-chromanone having the formula (II).

In the former pathway, 3-(4-fluorophenoxy)propionitrile having the formula (I) is stirred in polyphosphoric acid at a temperature of more than 140° C., preferably at about 170° C. for about 15 minutes to form 6-fluoro-4-chromanimine having the formula (V) and then the reaction mixture is poured into ice-water to hydrolyze 6-fluoro-4-chromanimine having the formula (V) into 6-fluoro-4-chromanone having the formula (II). Though this pathway comprises a short and simple step, it accompanies the side reaction with coloration. In the latter pathway, 3-(4-fluorophenoxy)propionitrile having the formula (I) is hydrolyzed with acid such as hydrochloric acid, hydrobromic acid and sulfuric acid into 3-(4-fluorophenoxy)propionic acid having the formula (IV). When hydrobromic acid or sulfuric acid is employed in a high concentration in order to increase the rate of hydrolysis reaction, an unfavourable side reaction such as cleavage of the ether bond and sulfonation of the aromatic ring may occur. On the other hand, when hydrochloric acid is employed, such side reaction as mentioned above does not occur. Concentrated hydrochloric acid is preferably used from the view point of the reaction rate and yield and 3-(4-fluorophenoxy)propionitrile having the formula (I) is refluxed in the concentrated hydrochloric acid for 10 hours to give 3-(4-fluorophenoxy)propionic acid having the formula (IV) in a quantitative yield. Cyclization of 3-(4-fluorophenoxy)propionic acid having the formula (IV) into 6-fluoro-4-chromanone having the formula (II) can be carried out in a good yield by known method where the compound (IV) is stirred in polyphosphoric acid at 100° C. for 10 minutes (U.S. Pat. Nos. 4,117,230 and 4,130,714), or by the method where the compound (IV) is treated in concentrated sulfuric acid. If the condition of acid hydrolysis and ring closure reaction is agreed, 6-fluoro-4-chromanone having the formula (II) can be obtained in an almost quantitative yield from 3-(4-fluorophenoxy)propionitrile having the formula (II). When 3-(4-fluorophenoxy)propionitrile having the formula (I) is stirred in 85 to 95% sulfuric acid at 90° C. for 10 hours, hydrolysis reaction and ring closure reaction occur simultaneously and thus 6-fluoro-4-chromanone having the formula (II) can be obtained directly. In this reaction, however, by-product such as 3-(4-fluorophenoxy)propionic acid is formed and the yield is quite low.

The present invention is more particularly described and explained by the following Examples. However, it is to be understood that the present invention is not limited to the Examples, and various changes and modifications may be made without departing from the scope and spirit of the invention.

EXAMPLE 1

A mixture of 11.2 g of 4-fluorophenol, 26.5 g of acrylonitrile and 4.9 g of cupric hydroxide was refluxed for 8 hours with stirring, and then acrylonitrile and 4-fluorophenol were removed from the mixture under reduced pressure. After diluting the obtained residue with ether and filtering solid, the ether layer was successively washed with 10% aqueous solution of sodium hydroxide and 2N hydrochloric acid and dehydrated with anhydrous magnesium sulfate. Ether was distilled away to give 14.02 g of colorless liquid of 3-(4-fluorophenoxy)propionitrile (yield: 85%).

IR (cm$^{-1}$): 2250, 1500, 1250, 1200, 830 and 740.

$^1$H NMR(CDCl$_3$, δ): 7.13 to 6.67 (m, 4H), 4.13 (t, 2H) and 2.80 (t, 2H).

Elementary Analysis for C$_9$H$_8$FNO: Calcd.: C 64.45%, H 4.88%, N 8.48%. Found: C 65.27%, H 5.01%, N 8.60%.

EXAMPLE 2

A mixture of 11.2 g of 4-fluorophenol, 10.6 g of acrylonitrile and 2.02 g of triethylamine was refluxed for 16 hours with stirring and then acrylonitrile, triethylamine and 4-fluorophenol were removed under reduced pressure. The obtained residue was diluted with ether, washed successively with 10% aqueous solution of sodium hydroxide and 2N hydrochloric acid and dehydrated with anhydrous magnesium sulfate. Ether was distilled away to give 11.51 g of colorless liquid of 3-(4-fluorophenoxy)propionitrile (yield: 70%).

EXAMPLE 3

A mixture of 1.12 g of 4-fluorophenol, 2.65 g of acrylonitrile and 5 mmol of cupric hydroxide was reacted for 10 hours at a reflux temperature of acrylonitrile with stirring. After completion of the reaction, a yield of 3-(4-fluorophenoxy)propionitrile based on 4-fluorophenol was measured by gas liquid chromatography (Hitachi 063 gas chromatograph; column: FAL-M (chromosorb W (AM-DMCS) H$_3$PO$_4$, 3 mm×1 m)) and was 89%.

The same procedures as above were conducted except that various kinds of catalyst were employed in various amounts. The results are shown in Table 1.

TABLE 1

| Run | Catalyst | Amount of catalyst (mmol) | Yield (%) |
|---|---|---|---|
| 1 | Cu(OH)$_2$ | 5 | 89 |
| 2 | Cu(OAc)$_2$ | " | 50 |
| 3 | Cu(OAc)$_2$.H$_2$O | " | 76 |
| 4 | CuCO$_3$.Cu(OH)$_2$.H$_2$O | " | 59 |
| 5 | CuO | " | 20 |
| 6 | Cu (powder) | " | 59 |
| 7 | Ca(OH)$_2$ | " | 17 |
| 8 | Ba(OH)$_2$.8H$_2$O | " | 52 |
| 9 | Zn(OH)$_2$ | " | 45 |
| 10(*) | Me$_3$N | 2 | 60 |
| 11 | Et$_3$N | " | 76 |
| 12 | (n-Bu)$_3$N | " | 68 |
| 13 | (n-Oct)$_3$N | " | 68 |
| 14 | HDMA (Cyclohexyl dimethyl amine) | " | 72 |
| 15 | Triton B | 0.3 | 39 |
| 16 | None | — | 0 |

Note: (*) The reaction was carried out in an autoclave at 60° C.

EXAMPLE 4

A mixture of 45.50 g of 3-(4-fluorophenoxy)-propionitrile and 70 ml of 12N hydrochloric acid was stirred for 10 hours at about 120° C. After cooling and distributing the mixture to ethyl acetate/water, an ethyl acetate layer was separated and dehydrated with anhydrous magnesium sulfate. Ethyl acetate was distilled away to give 50.70 g of a white crystal of 3-(4-fluorophenoxy)propionic acid.

mp: 84° to 85° C. (A value described in a literature is 86° C.)

IR and $^1$H NMR values were agreed with those of samples synthesized from 4-fluorophenol and 3-chloropropionic acid by the conventional process.

EXAMPLE 5

A mixture of 30.0 g (163.0 mmol) of 3-(4-fluorophenoxy)propionic acid and 180 ml of concentrated sulfuric acid was stirred for 1 hour at room temperature and then the reaction mixture was poured into 700 g of ice to deposit immediately a white crystal. The white crystal was collected by filtration, washed with water and dried in air, and the resultant was recrystallized from ethanol to give 20.55 g of 6-fluoro-4-chromanone as a white crystal (yield: 76%).

mp: 113° to 115° C. (A value described in a literature is 114° to 116° C.)

EXAMPLE 6

A mixture of 2.00 g of 3-(4-fluorophenoxy)propionitrile and 40 g of 85% sulfuric acid was stirred for 10 hours at 90° C. After cooling, the reaction mixture was poured into a proper amount of ice-water and extracted with ethyl acetate. After an ethyl acetate layer was neutralized with 20% aqueous solution of sodium hydroxide, the layer was dehydrated with anhydrous magnesium sulfate. Ethyl acetate was distilled away to give 861 mg of a white crystal of 6-fluoro-4-chromanone (yield: 43%).

mp: 113° to 115° C. (A value described in a literature is 114° to 116° C.)

EXAMPLE 7

There was added 5.0 g of 3-(4-fluorophenoxy)propionitrile to 50 g of polyphosphoric acid warmed at 100° C. and the reaction temperature was raised to 170° C. for 10 minutes with stirring. After further stirring for about 10 minutes, the reaction mixture was poured into 200 ml of ice-water and stirred for about 1 hour. The resultant was extracted with ethyl acetate and the ethyl acetate layer was washed successively with 20% aqueous solution of sodium hydroxide and water and dehydrated with anhydrous magnesium sulfate. Ethyl acetate was distilled away to give 1.62 g of a brown crystal of 6-fluoro-4-chromanone (yield: 32%).

mp: 112° to 114° C. (A value described in a literature is 114° to 116° C.)

What we claim is:

1. A process for preparing 3-(4-fluorophenoxy)propionitrile having the formula (I):

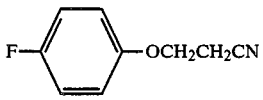

which comprises reacting 4-fluorophenol with acrylonitrile in the presence of a tertiary amine.

2. A process for preparing 6-fluoro-4-chromanone having the formula (II):

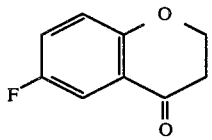

which comprises reacting 3-(4-fluorophenoxy)propionitrile having the formula (I):

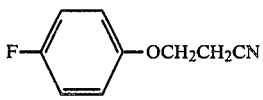

with 85 to 95% sulfuric acid.

3. A process for preparing 6-fluoro-4-chromanone having the formula (II):

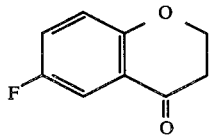

which comprises reacting 3-(4-fluorophenoxy)propionitrile having the formula (I)

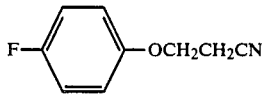

with polyphosphoric acid to give 6-fluoro-4-chromanimine having the formula (V):

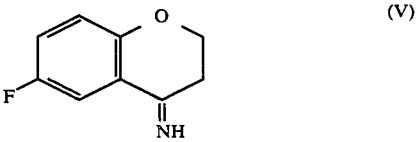

which is then hydrolyzed.

4. A process for preparing 6-fluoro-4-chromanone having the formula (II):

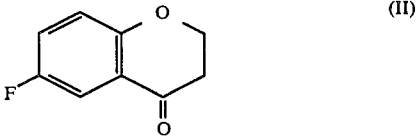

which comprises reacting 4-fluorophenol with acrylonitrile in the presence of a tertiary amine to give 3-(4fluorophenoxy)propionitrile having the formula (I):

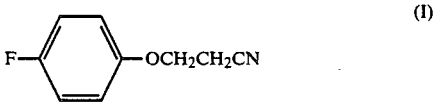

which is then reacted with an acid.

5. The process of claim 4, wherein said acid is polyphosphoric acid.

6. The process of claim 4, wherein said acid is 85 to 95% sulfuric acid.

* * * * *